(12) United States Patent
Ritsche et al.

(10) Patent No.: US 6,427,684 B2
(45) Date of Patent: Aug. 6, 2002

(54) DISCHARGE APPARATUS FOR MEDIA

(75) Inventors: Stefan Ritsche; Karl-Heinz Fuchs, both of Radolfzell (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 0 days.

(21) Appl. No.: 09/780,856

(22) Filed: Feb. 9, 2001

(30) Foreign Application Priority Data

Feb. 12, 2000 (DE) .......................................... 100 06 368

(51) Int. Cl.⁷ ................................................. B17D 5/32
(52) U.S. Cl. ............................ 128/200.23; 128/204.21; 222/153.14; 222/321.6; 222/642
(58) Field of Search ........................ 222/153.14, 321.6, 222/642, 183; 128/200.23, 204.21

(56) References Cited

U.S. PATENT DOCUMENTS

| | | | |
|---|---|---|---|
| 2,954,904 A | | 10/1960 | Potoczky |
| 4,871,092 A | * | 10/1989 | Maerte .................. 222/153.14 |
| 4,921,142 A | | 5/1990 | Graf et al. .................. 222/162 |
| 4,934,568 A | * | 6/1990 | Fuchs .................... 222/321.06 |
| 4,944,429 A | * | 7/1990 | Bishop et al. ......... 222/153.14 |
| 4,969,584 A | | 11/1990 | Joulia |
| 5,038,964 A | | 8/1991 | Bouix |
| 6,234,366 B1 | | 5/2001 | Fuchs ......................... 222/643 |

FOREIGN PATENT DOCUMENTS

| | | |
|---|---|---|
| DE | 44 47 087 | 7/1996 |
| FR | 2.152.479 | 9/1971 |
| FR | 2 657 795 | 8/1991 |
| WO | 98/55378 | 12/1998 |

\* cited by examiner

Primary Examiner—Philippe Derakshani
(74) Attorney, Agent, or Firm—Quarles & Brady LLP

(57) ABSTRACT

The problem of the invention is to so further develop a discharge apparatus according to the preamble that it is possible during each individual actuating stroke to reliably discharge a predetermined volume of medium.

A discharge apparatus for media according to the invention has a casing, on which is located an actuator. During each actuator actuation an actuating stroke takes place and consequently a given volume of the medium stored in the casing is discharged. According to the invention the gravity dependently operating blocking means are constructed in such a way that they can block the performance of an actuating stroke as a function of the spatial position of the discharge apparatus.

14 Claims, 7 Drawing Sheets

DISCHARGE APPARATUS FOR MEDIA

BACKGROUND OF THE INVENTION

Discharge apparatuses for media, which are in particular suitable for spraying a fluid preferably containing at least one pharmaceutical substance are generally known. Such a discharge apparatus on which the preamble is based can e.g. be gathered from DE 197 53 147 A1.

Such a discharge apparatus has a casing, an actuator being movable relative to said casing. With each actuator stroke a discharge process takes place and during each discharge process a specific fluid quantity is discharged from the container located in the casing.

Particularly when using such discharge apparatuses in conjunction with pharmaceutical substances, it is important that the same medium quantity is discharged during each actuating stroke. Since during the actuations of the actuator an ever greater air quantity collects in the medium container it is no longer necessarily ensured with decreasing medium supply that in each dispenser actuating position only medium is discharged in the discharge apparatus. There can also be secondary air suction, so that a smaller medium quantity and therefore a smaller substance quantity is discharged. This is particularly disadvantageous if it is necessary to ensure a very precise dosage of the active substance not only during a single actuation, but also over several actuations. This problem more particularly arises if it is necessary to wait a certain minimum period between two successive applications of the medium.

It can also be advantageous in other cases for the orientation of the discharge apparatus with respect to the environment to be fixed, so that a correct application or administration is ensured.

The problem of the invention is to further develop the discharge apparatus according to the preamble in such a way that it is possible to ensure the discharge of a predetermined medium volume during each individual actuating stroke.

SUMMARY OF THE INVENTION

A discharge apparatus according to the invention for media has a casing on which is located an actuator. During each actuation of the actuator an actuating stroke takes place and consequently a specific volume of the medium stored in the casing is discharged. According to the invention gravity dependently operating arresting or blocking means are constructed in such a way that as a function of the spatial position of the discharge apparatus they can block or arrest the performance of an actuating stroke.

According to a preferred development of the invention the gravity dependently operating arresting means are movably mounted, mechanically acting operating or switching means, which are preferably so guided that under a predetermined spatial orientation of the discharge apparatus, said operating means block an actuating stroke of the actuator. The operating means are preferably balls guided in a cam or curved path and whose diameter is advantageously smaller than the path of an actuating stroke of the actuator and preferably the diameter of a ball almost corresponds to the path of an actuating stroke.

According to a preferred development of the invention the curved path at least approximately is in the form of an inclined plane. Preference is also given to a construction in which the curved path has at least one dwell trough defining a holding position and intended to receive the balls. It is also preferable for the dwell trough to be positioned in the vicinity of the curved path in which the balls block an actuating stroke of the actuator.

According to an advantageous development of the invention at least two operating means movable in different, independent directions are provided. The operating means are preferably constructed in such a way that they in each case have on one side a stop member and on the side of the operating means remote from the stop member is constructed the position blocking the actuating stroke of the actuator and where in each case a pair of operating members is provided, whose stop member is constructed on opposite sides of the movement path. Preferably the operating means of a pair are oriented in a common direction and formed on opposite sides of the discharge apparatus.

Preference is also given to a construction in which the blocking means block an actuating stroke, if the divergence of the discharge direction of the discharge apparatus from the vertical exceeds an angle of at least 30.

BRIEF DESCRIPTION OF THE DRAWINGS

The invention is described in greater detail relative to embodiments illustrated in the attached drawings, wherein:

FIGS. 3a–3e are views of a locking cap according to the invention with a connecting link guide;

DETAILED DESCRIPTION OF A PREFERRED EMBODIMENT

Figure 1:
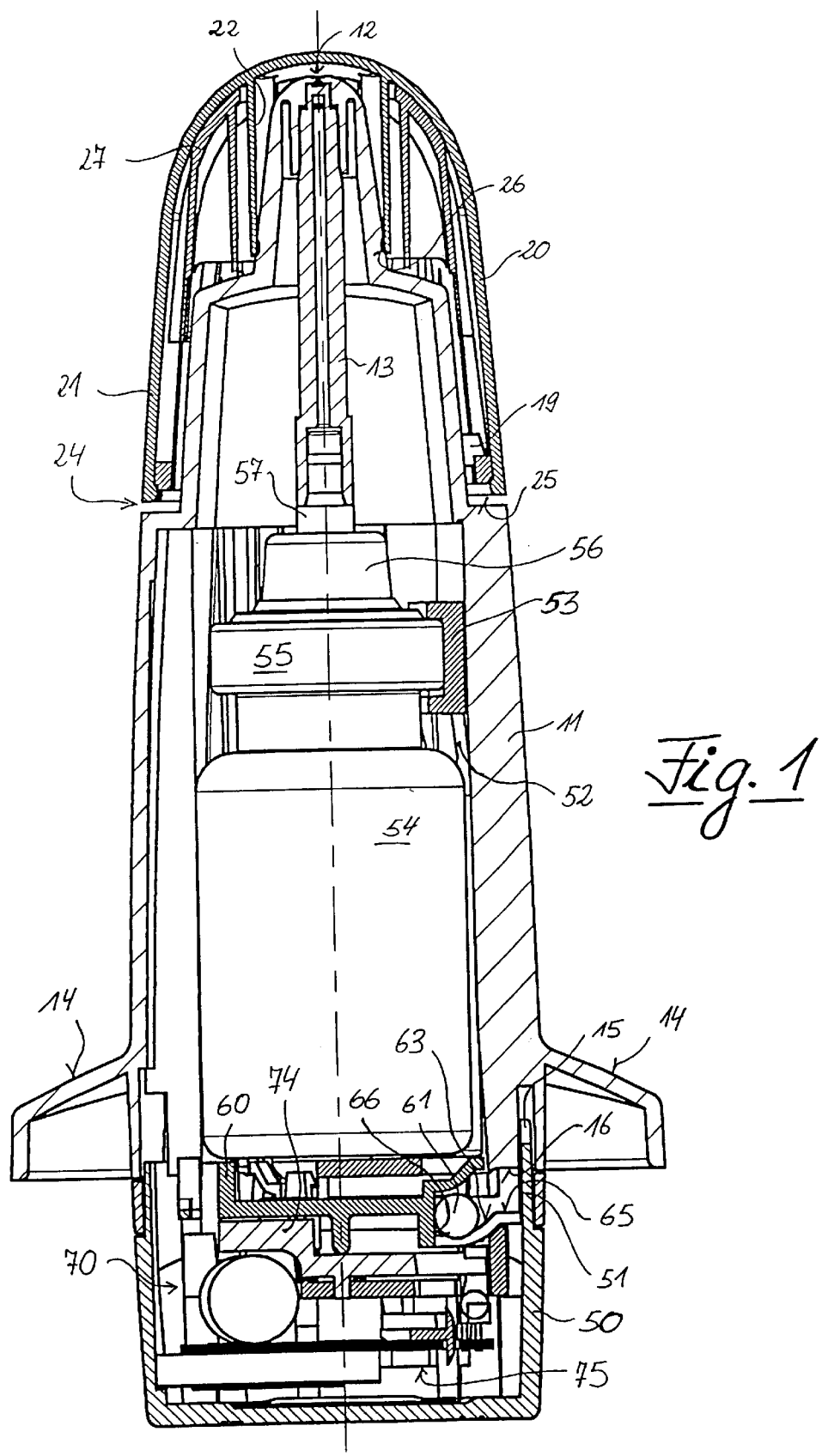
FIG. 1 is a partial sectional view of discharge apparatus for media according to the present invention.

FIG. 1 shows in a part sectional representation a discharge apparatus for media, such as can in particular be used for spraying a fluid, which preferably contains a pharmaceutical substance.

The discharge apparatus has a casing 11 containing in a manner sealed from the outside the functional elements. For the discharge of the medium, particularly a fluid, the casing has a discharge opening 12. In order to prevent dirtying in the vicinity of the discharge opening 12 and consequently a possible infection or contamination with bacteria, the casing is closed with the locking cap 20 mountable thereon in locking manner. The locking cap 20 is formed by an outer part 21 and an inner part 27. Between the lower edge of the locking cap 25 and the associated casing section is left a narrow gap 24. Otherwise the casing 11, together with the fitted locking cap 20, forms a substantially uniform, closed surface. The outer part 21 of the locking cap also has the shaped section, which is here in the form of a hollow cylinder and is placed from the inside on the closed surface 23 of the outer part 21 and projects into the inner part 27 of the locking cap 20. The shaped section 22 surrounds the casing 11 in the area containing the discharge opening 12 and sealingly engages on the casing in the vicinity of the bearing surface 26. This ensures that no air from the outside can be exchanged with that in the hollow cylindrical portion of the shaped section 22, which is closed by the sealing bearing surface 26 on the casing. This prevents contamination or infection of the casing 11 in the vicinity of the discharge opening 12. The inner part 27 of the locking cap 20 has a connecting link guide 28 for the slider 19 constructed on the casing 11 and which is not visible in this part sectional representation.

On its end remote from the locking cap 20 the casing 11 has gripping surfaces 14, which can be used for holding the casing 11 when the discharge apparatus is in use. The casing is opened at its lower end and is closed by the actuator 50. For guiding the actuator 50 in the casing 11 an annular groove 15 is formed in the casing and in it is immersed during actuation the corresponding immersion web 51 of the actuator. The path of an actuating stroke of the actuator is fixed in cooperation between the depth of the annular groove 15 of the casing 11 and the length of the immersion web 51 on the actuator 50. In the selected construction according to the invention the actuating stroke is limited in that the immersion web 51 abuts on the bottom of the annular groove 15. In the non-actuated position of the actuator 50 there is consequently a gap between said actuator 50 and the casing 11. This gap can be closed with anti-tampering means, having predetermined breaking points and therefore removable.

The spacer 13 is positionally fixed with the casing 11, leads to the discharge opening 12 and contains the discharge channel. The length of the spacer 13 is determined through the space remaining in the casing 11 as a function of the size of the container 54. The larger the container 54, the more actuations of the actuator 50 can be performed before the container 54 is emptied. The spacer 13 is positionally fixed with respect to the casing 11. The container 54 is positionally fixed on the actuator 50. The container 54 is closed by the suction pump 56 by means of the crimp ring 55. The plunger 57 of the suction pump 56 is constructed in such a way that it bears on the spacer 13 and for the discharge of the medium a through channel is formed through the plunger 57 and spacer 13 to the discharge opening 12. The container 54 is fixed to the support member 52 by means of the holder 53 acting on the crimp ring 55. The support member 52 is in turn at least indirectly fixed to the actuator 50.

In the vicinity of the lower seal of the casing 11, which is formed by the stop face 16, the guide ring 60 is located in the actuator 50 in the form of a mechanically constructed operating means of a gravity dependently operating blocking means. In the guide ring 60 there are several and in the represented embodiment three cam or curved paths 62 in each case mutually displaced by 120° and in which is guided a ball 61. However, FIG. 1 only shows one curved path 62. At its inner end the curved path 62 has the stop face 66 against which the ball 61 engages in this orientation of the discharge apparatus. In this position the balls permit the performance of anactuating stroke of the actuator 50. Apart from its end stop 66, the curved path has a ramp in the form of an inclined plane 63, which has the inclination angle 64 with respect to the horizontal. This inclination angle determines as from which inclination of the discharge apparatus the balls guided in the curved path 62 can roll on the ramp and finally pass into the other, outer end position formed by the dwell trough 65. In the dwell trough 65 the balls 61 are beld between the guide ring 60, which is firmly fastened to the actuator 50 and the stop face 16 of the casing 11. As the ball diameter at least approximately corresponds to the actuating path of anactuating stroke, if the balls 61 are in this position an actuation of the actuator is blocked. There can be two or four curved paths 62 instead of three. If two curved paths are provided, they must be constructed in such away that they operate in double-sided manner, i.e. determining an inclination with respect to the privileged direction in which the discharge apparatus is to be oriented, usually the vertical direction, in one direction on bothsides. All that is important is that the curved paths 62 can determine the inclination in a random direction with respect to the privileged direction, i.e. with resolution into at least two independent directional components.

The actuator 50 also contains the control unit 70, which incorporates a time determination and a determination of the actuations of the actuator. The control unit is able to switch backwards and forwards the blocking member 74 between a release position 71 and a blocking position by means of the electromagnet 75, which is controllable by the control unit 70 and which can act on the blocking nember 74.

Figure 2B:
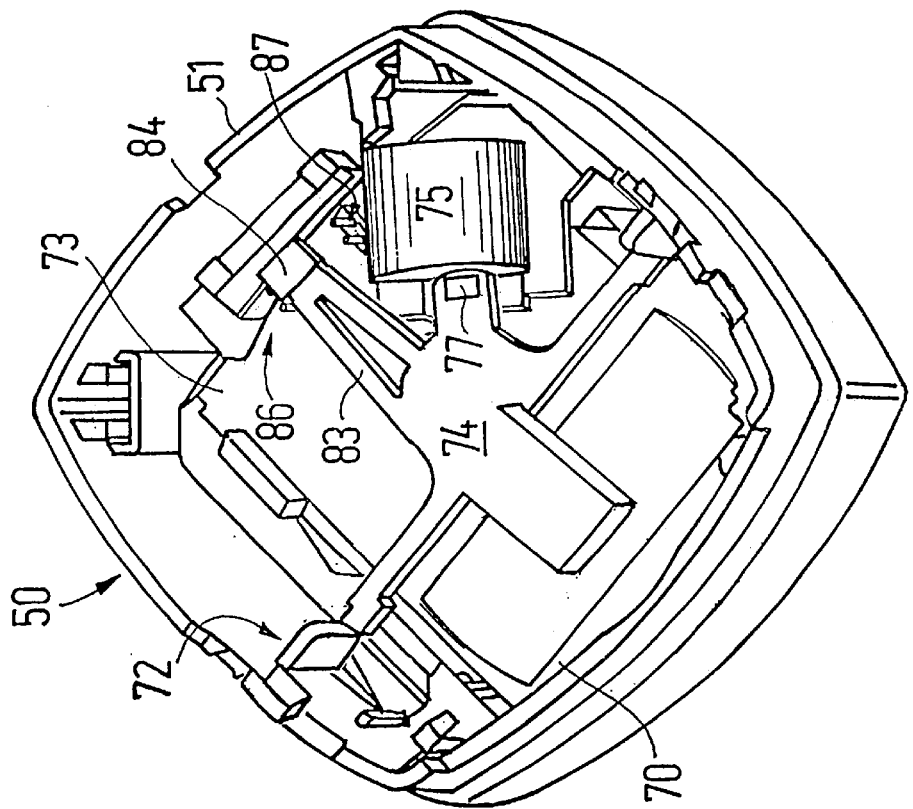
FIGS. 2a–2e are views of the control unit which is located in the actuator with the controllable actuating stop in the release position and in the blocking position.
Figure 2A:
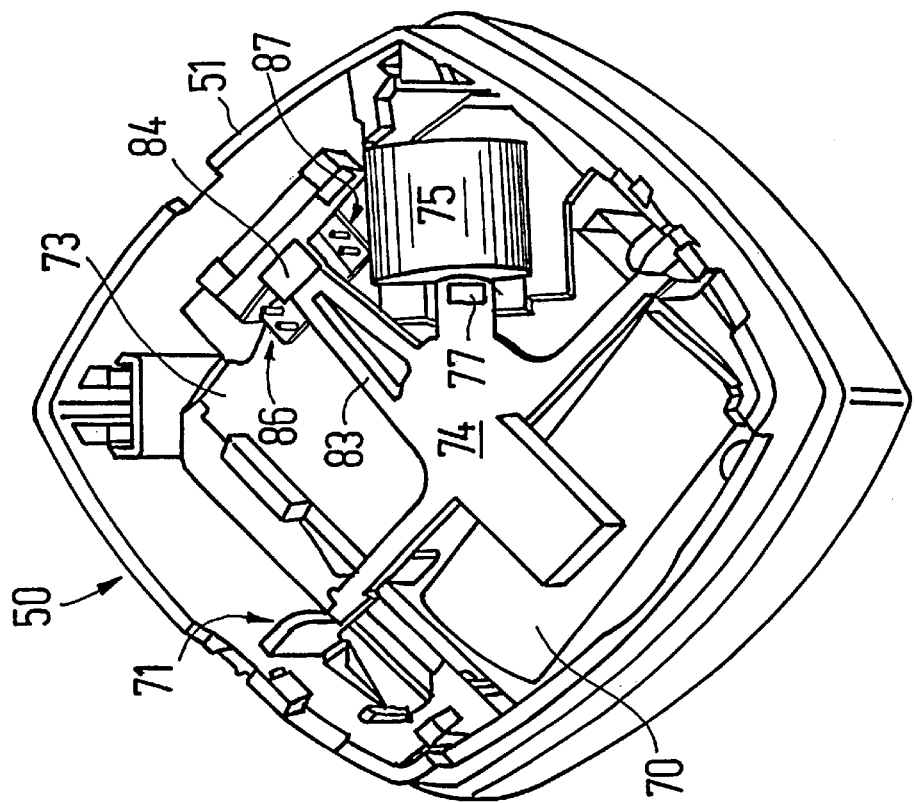

FIGS. 2a and 2b show a view of the actuator 50 with the actuating stop located therein. The actuating stop is formed by the control unit 70, the electromagnet 75 and the blocking member 74. Preferably said elements are placed on a common base plate 73, which is preferably fixed by locking in the actuator 50.

FIG. 2a shows the blocking member 74 in the release position 71 of the actuating stop, whereas in FIG. 2b which otherwise corresponds to FIG. 2a, the blocking member 74 is in the blocking position 72 of the actuating stop.

The power supply, which is not shown in the drawings, is provided by means of a battery, greferably a button cell or the like and is e.g. positioned below the base plate 73. The power supply can be buffered with acapacitor, which e.g. permits the maintaining of the stored values during a battery change or allows a final actuation of the actuator 50 by the battery after a failure of the power supply. The base plate 73 is preferably simultaneously constructed as a blank having the corresponding electric lines, which in particular include the electrical connections between the control unit 70 and the electromagnet 75, which is also located on the base plate 73. It acts or a magnetic body 77 constructed on the blocking member 74. The magnetic body 77 is used, under the influence of the electromagnetic forces acting between said body 77 and the electromagnet 75 constructed as a current relay, to produce a changeover movement of the blocking member 74. The blocking member 14 in the embodiment shown can be brought by pivoting about its center axis from the release position 71 into the blocking position and vice versa.

Figure 2C:
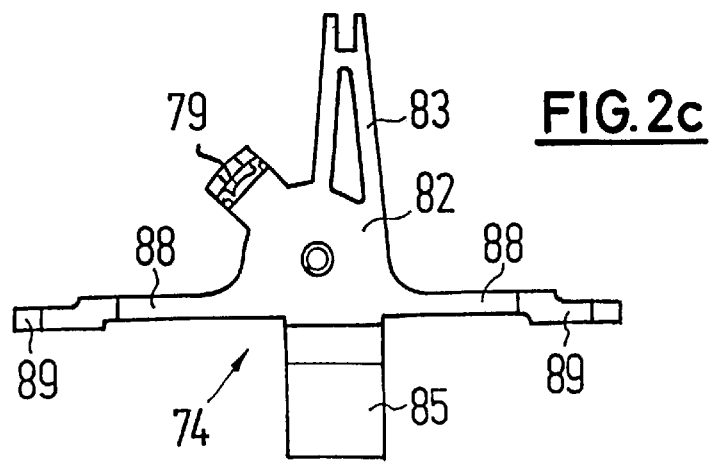
Figure 2D:
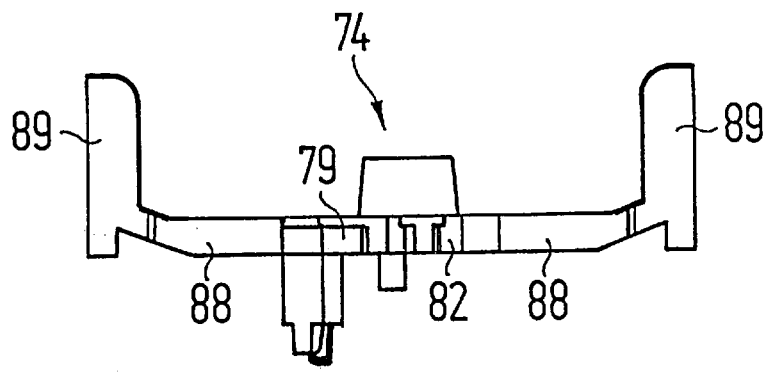

A detailed drawing of the blocking member 74 is shown in plan view and side view in FIGS. 2c and 2d respectively.

For determining the position of the blocking member 74 on the latter is constructed a holding arm 83, on whose end is provided a contact piece 84. On either side of the contact piece 84 on the base plate 73 are provided first and second contact pin pairs 86, 87.

In the release position 71 shown in FIG. 2a by means of the contact piece 84 the electrical connection between the two contact pins of the second contact pin pair 87 is closed and consequently a signal is generated for the control unit 70 indicating that the blocking member 74 is in fact in the release position 71. If the blocking member 74 is brought by the action of the electromagnet 75 into the blocking position shown in FIG. 2b, the contacting of the second contact pin pair 87 is interrupted by means of the contact piece 84 and at the end of actuation the electrical connection of the contact pins of the first contact pin pair 86 is restored by means of the contact piece 84. Thus, a signal is generated for the control unit 70 indicating that the base plate 73 is in the blocking position 72. At the same time it is possible to provide the blocking body 89 on its casing-side face with a colour marking detectable by means of a casing-side viewing window and providing optical information on the operating position of the blocking member (e.g. green=release position/red=blocking position).

Figure 2E:
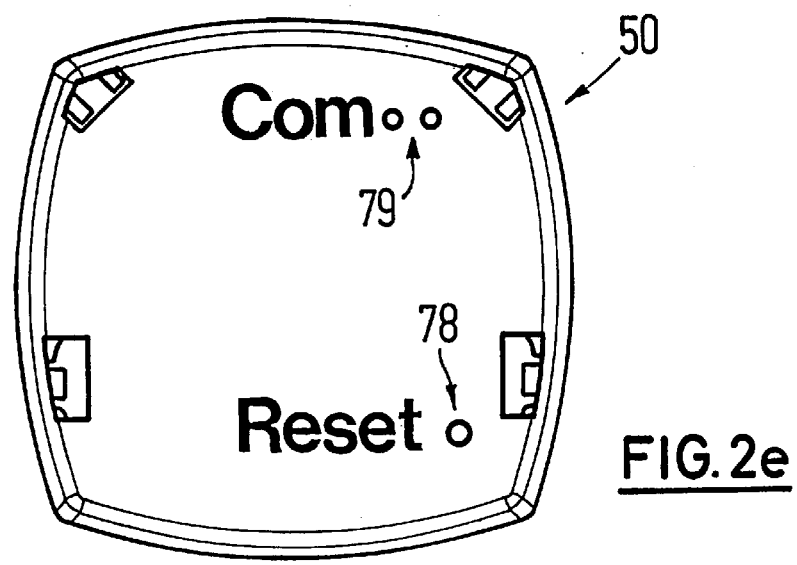

FIG. 2e is a view from below of the outside of the casing of the actuator 50, which has on its base surface 58 the switch 78 and the interface 79. The switch 78 can in particular be constructed as a countersink keying switch, whose operation is performed e.g. by an auxiliary means, preferably a sharp object, e.g. a pencil point. The interface 79 is placed on the base surface 58. The interface 79 is used for contacting an information medium with the control unit 70. The information medium can either be a passive component, in the sinplest case a contacting bridge or an input/output unit, such as e.g. a PC, by means of which data, preferably parameters for the function of the control unit 70, can be transmitted thereto and information can also be read out of the control unit. The parameters which can be transmitted to the control unit 70 are in particular the value of the first time interval beginning when an actuation of the actuator takes place and which establishes the time period which must elapse before the next actuation of the actuator, so that no actuation blocking takes place. The second time interval can also be transferred as a parameter into the control unit 70. The second time interval determines the time during which, after operating the switch 78, a predetermined number of actuator actuations can be carried out without the actuating stop coming into action. It is also possible to preset by means of the interface 79 said number of actuations which can be performed without intervention of the actuating stop following operation ofthe switch 78. The interface 79 can in particular be a plug connection of a data bus for the control unit 70. Two-wire data buses can be used. It is also possible to read out information from the control unit 70 via the interface 79. It is e.g. possible to determine the number of actuating strokes which have taken place, together with the number of actuations of the switch 78. It is also possible to determine how often the actuator has actuated before the end of the first time interval after the preceding actuation of the actuator. This information can be looked upon as a measure of the need for a patient to receive a higher active substance dose administration. It is possible to fix in accordance with needs the parameters which are to be preset and the information which is to be read out of the control unit 70. Due account must be taken of this when designing the control unit 70.

In a simpler construction the information element can be constructed merely as a contact bridge for electrical contacting between the two individual wires terminating at the interface 79. Preferably the contact bridge is in the form of a specially shaped plug only suppliable e.g. to limited numbers of people, such as nurses and pharmacists. If the presence of the bridge plug at the interface 79 is required when the switch 78 is operated, in this way it is possible to ensure that unauthorized persons cannot perform a number of actuations of the actuator 50 without the actuating stop coming into action. This ensures an increase in operating reliability. However, it can also make it necessary that the first putting into operation of the discharge apparatus takes place by an authorized person.

FIGS. 2c and 2d are a plan view and side view of the blocking member 74. In its centre 82 the blocking member 74 is in the form of a disk rotatable about the centre axis 80. From the centre projects to the outside the holding arm 83, which is constructed at its end for receiving the contact piece 84 and also the permanent magnetic body 77. Facing the magnetic body 77 and holding arm 83 is constructed the counter weight 85, which ensures an at least approximate balancing of the blocking member 74 with respect to the center axis 80 and consequently easy operation of the blocking member 74. Two arms 88 located on an axis eccentric to the centre axis 80 also project from the centre 82. The blocking bodies 89 are formed at the end of the arms 88. The blocking bodies project upwards parallel to the centre axis 80 in the actuator 50 out of the plane of the blocking member 74. The height of the blocking bodies 89 correspond to the path of an actuating stroke of the actuator 50. It is possible in the release position 71 of the blocking member 74 to introduce the blocking bodies 89 into the casing 11, e.g. in a guidance groove. In the blocking position 72 the blocking bodies 89 are positioned in such a way that they fill the gap between the lower end of the casing 11 with its stop face 16 and a correspondingly constructed face on the actuator. This prevents a sliding of the actuator by the path of the actuating stroke of the discharge apparatus, so that an operation of the latter is prevented. It must be borne in mind that a discharge apparatus of the type used here, i.e. in particular a pump atomizer, has a certain idle path. By this idle path at the most the blocking bodies 98 can be shorter than the path of the actuating stroke of the actuator 50. By pivoting about the centre axis 80, the blocking member 74 can be moved into the blocking position 72 and then back into the release position 71. At least for as long as the blocking bodies are not non-positively held in the casing, said movement can take place almost free from forces, e.g. if a person operates the actuator 50 and the blocking body 89 in its blocking position 72. Thus, an electromagnet producing low forces is adequate for very rapidly changing the operating position of the blocking member 74. No great force expenditure or energy expenditure are required. In particular, a changeover can take place in the short time period during which the idle path of the actuator 50 is covered during an actuation. It is possible in energy-saving manner with the blocking member 74 located in the release position 71 and in monostable form in the rest position, to produce the blocking position by brief operation of the electromagnet.

Figure 3B:
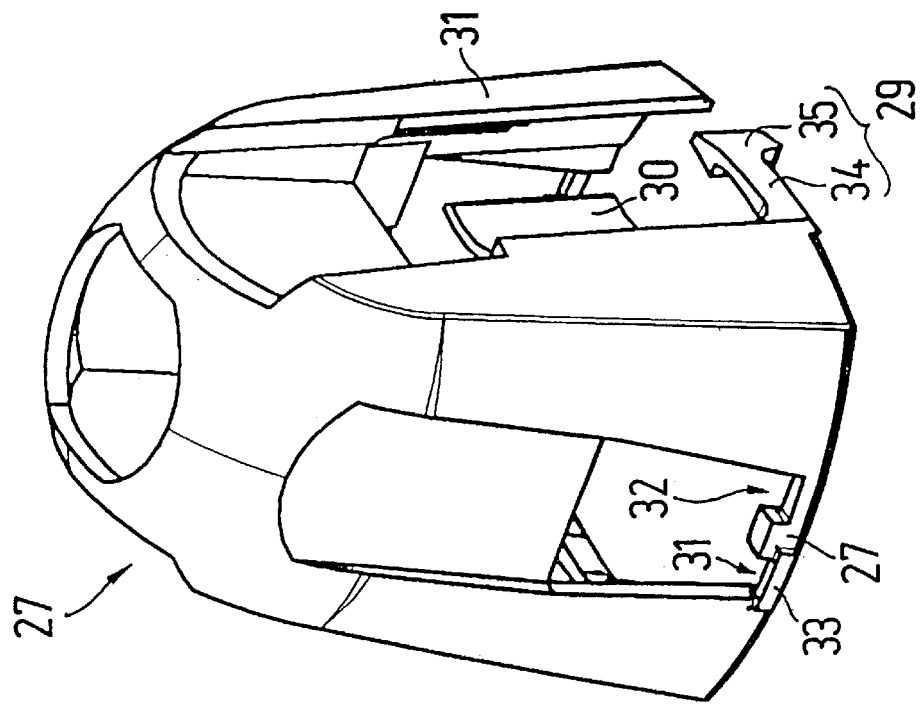
Figure 3A:
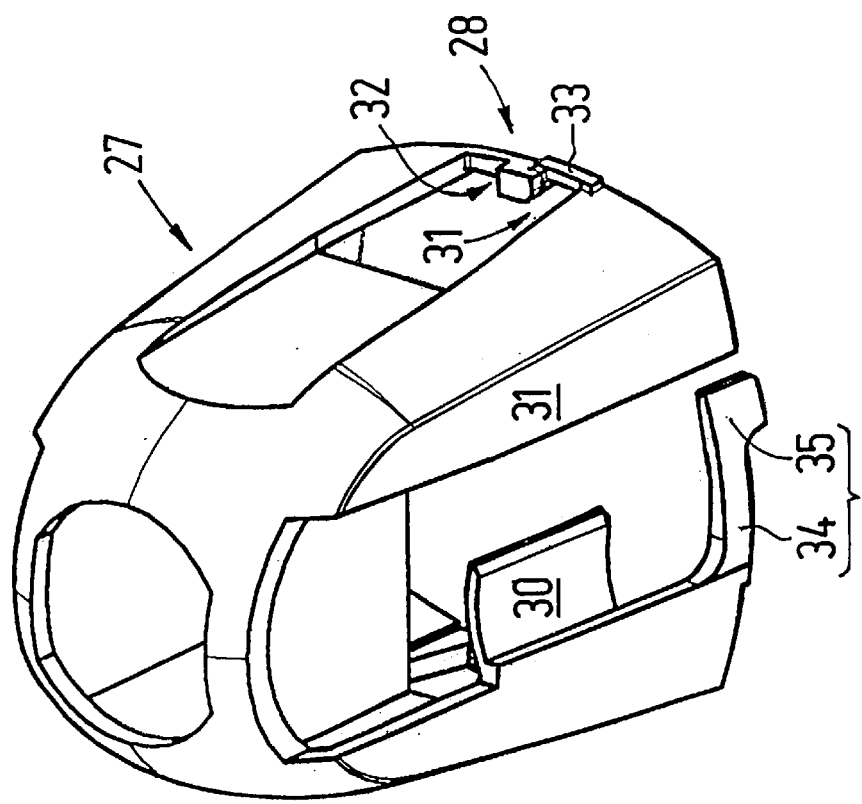

FIGS. 3a and 3b show from two different perspectives a view of the inner part 27 of the locking cap 20. The locking cap 20 is formed from the inner part 27 and the outer part 21 shown in FIG. 3c. The inner part 27 is formed by a basic body 31, which carries all the elements constructed for the function of the locken cap. For the construction of the connecting link guide 28 for the slieder 19 located an the casing a free space 31 is provided, which skirts a web. After crossing the web, it is possible to turn the locking cap by an angle, which is preferably smaller than 90° and in the represented embodiment is approximately 20°. The slider can then "drop" into the trough 32. The slider 19 is held in the trough 32 in such a way that a turning of the locking cap cannot take place directly out of this position. To ensure that the slider 19 securely enters the trough 32, an the inner part 27 the accumulator 29 is constructed in the form of a bendable material element, which is elastically deformable in the vicinity of the shank 34. The head 35 projects into the interior of the inner part and engages with the casing 11. As the inside of the head is bevelled in the same way as the casing 11 in this area, the head is pressed outwards, so that a force is built up if the inner part or the locking cap is placed an the casing 11. The bevel ensures that if no further force acts from the outside an the locking cap 20, the elastic deformation has a tendency to re-form and said force, supported an the casing, slides upwards the cap in the release direction an the casing 11. Thus, due to the intermediately effected rotation of the locken cap 20, the slider 19 of the casing enters the trough 32. The working element 30 is also formed an the inner part 27 and is also a material web elastically deformable within certain limits. On rotating the locking cap an the casing 11, the working element 30 engages with said casing shaped in non-round manner. During rotation the working element 30 is pressed outwards and slightly elastically deformed. Thus, a force counteracting the opening of the locking cap is built up. Simultaneously a certain force must be expended in order to place the locking cap on the casing. Operational reliability and safety is aided by the fact that the user of the discharge apparatus during actuation for opening purposes must apply a minimum force and also during the closing of the casing with the cap a force must be applied.

Advantageously on both opposite sides are formed connecting link guides 28 and between the same in each case an accumulator 29 and/or working element 30.

It is easy from the manufacturing standpoint to produce the locking cap from the inner part 27 and the outer part 21. However, it is also possible to have only a one-part locking cap, which then has a more complicated shape or towards the outside does not have a closed, smooth surface throughout.

Figure 3C:
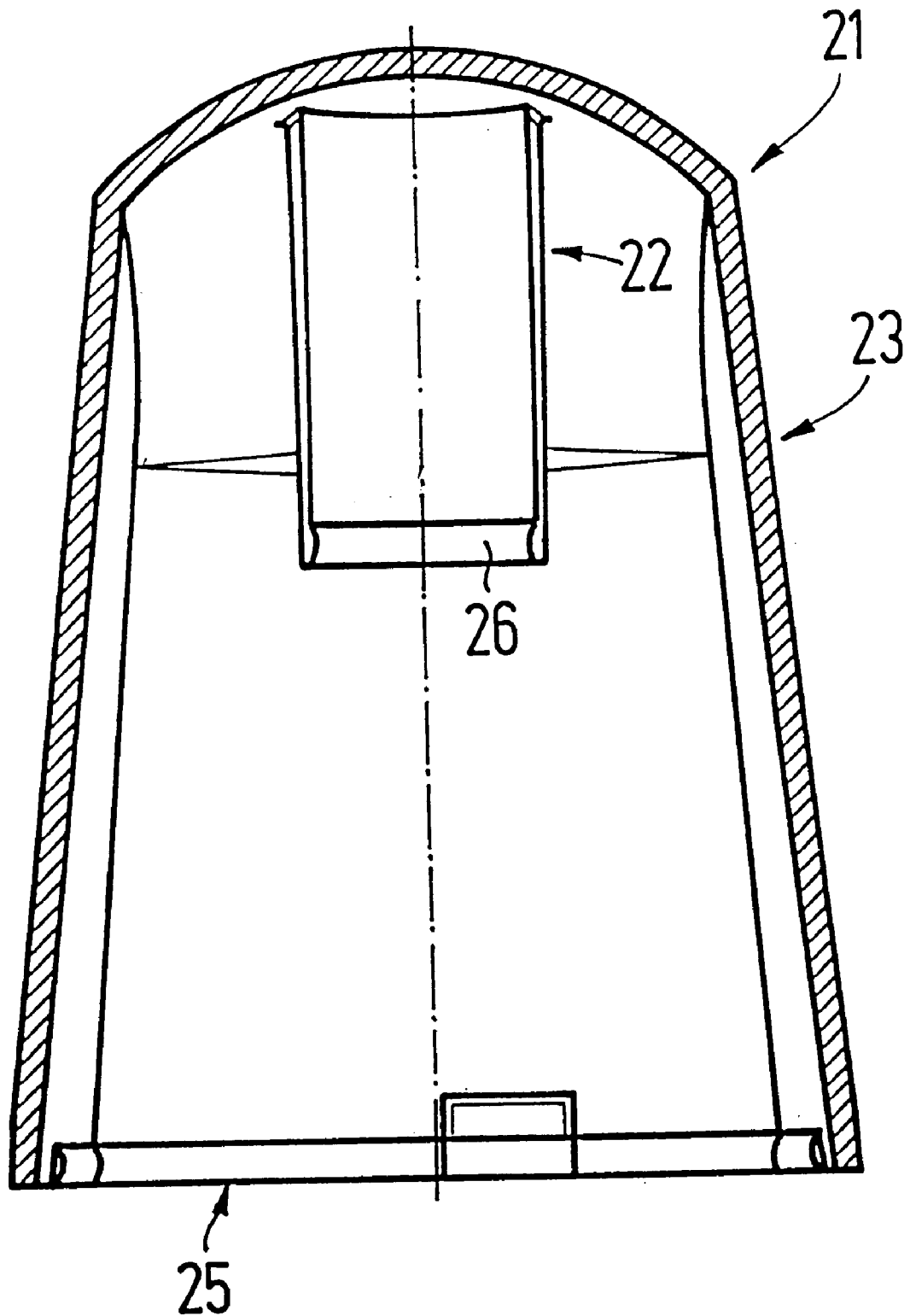

FIG. 3c shows the outer part 21 having a closed, smooth outer surface 23. Into the interior of the outer part 21 is introduced the inner part 27 and is positively or non-positively fixed there. The interior of the outerpart 21 also has the shaped section 22 in the form of a hollow cylinder. The shaped section 22 abuts by one end against the inside of the closed surface 23. On its other end is formed the sealing bearing surface 26, which bears on the casing 11 in such a way that the discharge opening 12 is surrounded.

On the outer part 21 is also formed the lower edge or border 28, on which can be supported a mandrel, not shown in the drawings, when the locking cap is placed on the casing 11. The mandrel is passed through an opening 11 in the casing and is firmly connected to the actuator 50. This ensures that there is no actuator of the actuator 50 when the locking cap is closed. This increases safety and in particular operational reliability in conjunction with the time-out during the first time interval following anactuation of the actuator 50, which can only take place when the locking cap has been removed.

Figure 4A:
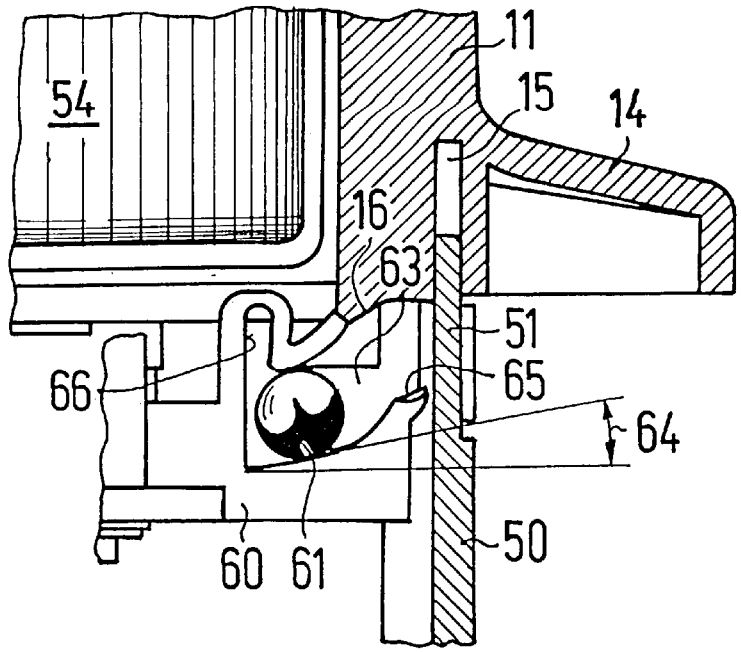
FIGS. 4a and 4b are views of a gravity dependent blocking mechanism in a position permitting actuation and in a position preventing actuation.
Figure 4B:
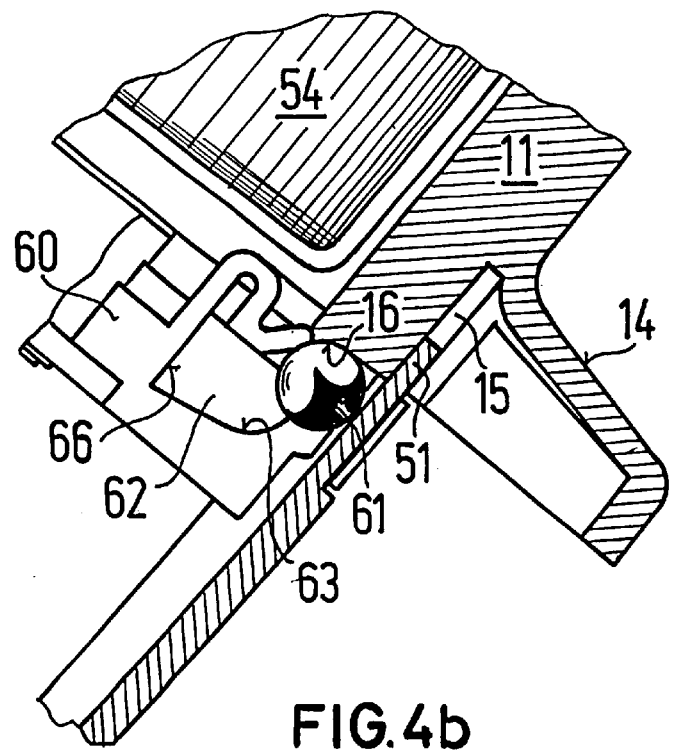

FIGS. 4a and 4b show the function of the guide ring 60 in two different positions. The guide ring 60 is fixed to the actuator 50 and is positioned in the vicinity of its upper end, i.e. the casing-side end. The casing 11 has the annular groove 11 in which the immersion web 51 of the actuator 50 is immersed during actuation. The guide ring is positioned in such a way that the curved path 62 for the balls 61 guided therein issues on the outside of the actuator 50 immediately below the stop face 16 on casing 11. The stop face 16 can be shaped in such a way that it takes over part of the guidance of the balls 61 in the curved path.

FIG. 4a shows the situation of the discharge apparatus when discharge is possible. This is preferably desired if the discharge apparatus is no longer inclined by a preset angle, preferably between 30 and 35°, with respect to the vertical (as the privileged direction). The balls 61 are guided in the curved path 62 of the guide ring 60. The curved path 62 has an inclined plane 63, so that in an almost vertical position the balls 61 are located on the inner end stop 66. It is possible in this position to perform an actuating stroke of the actuator. For this purpose it is merely necessary to move the actuator by the actuating path relative to the casing 11.

As soon as the inclination of the discharge apparatus exceeds an angle with respect to the vertical preset by the inclination 64 of the inclined plane 63, the balls roll in the curved path 62 until the outer end of said path is reached and abutment occurs on the actuator 50. Holding then takes place in the dwell trough 65 formed on the curved path 62. It is now located between the dwell trough 65, i.e. the guide ring 60 and the stop face 16 on the casing 11. As the balls 61 have a diameter approximately corresponding to the path of an actuating stroke, they block the performance of such a stroke, because the necessary free space between the dwell trough 65 and stop face 16 is filled by the balls. This prevents an actuation of the actuator 50 for as long as the inclination of the discharge apparatus with respect to the privileged direction is not within a preset angular position. The blocking position of the balls 61 is shown in FIG. 4b.

This ensures that during each discharge stroke the same medium quantity is discharged from the container 54. This is particularly important if a time-out is provided, which blocks a following actuation of the actuator 50. If an only inadequate partial quantity of medium is discharged during an actuation, it is not possible by a second actuation or second partial actuation to discharge the residual quantity or also a complete discharge quantity. This problem more particularly arises if a suction pump is used for discharge purposes. It is possible with such suction pumps if the container inclination exceeds a certain angle, for no complete medium suction to occur and instead for a partial secondary air volume to be sucked in and discharged.

Figure 5:
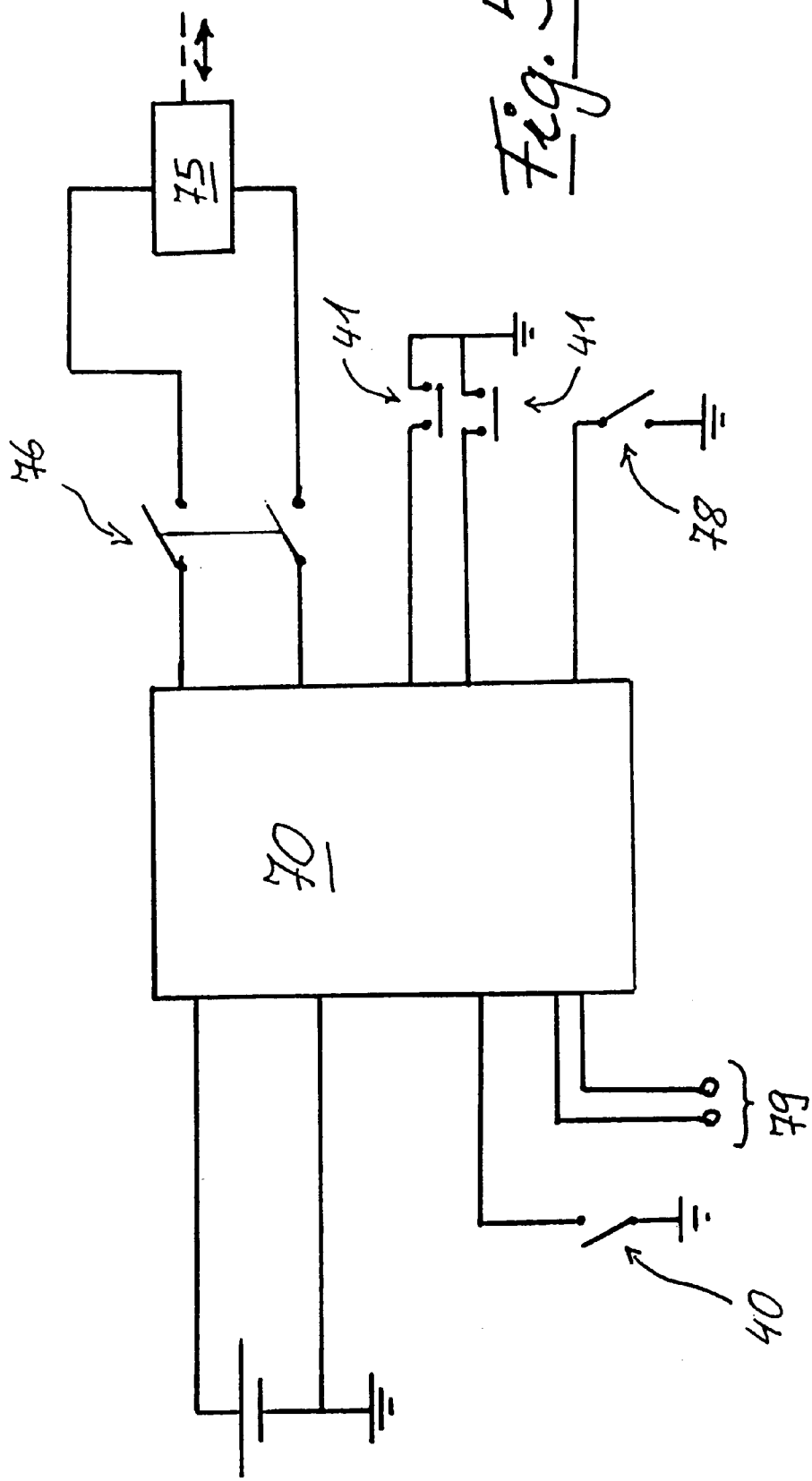
FIG. 5 is a block diagram of a circuit for the control unit and the actuating stop actuated by it.

FIG. 5 shows the diagram for a medium discharge apparatus according to the invention with an actuating stop controllable by a control unit. For actuating the actuator the electromagnet 75 is provided and controlled by the control unit 70.

If the control unit is energized for the first time, i.e. a battery for power supply purposes is fitted on the side of the actuator, or removal takes place by the user of a contact protection from the battery or the contact elements forming the electrical contact with the battery, the control unit permits the performance of a predetermined number of actuations of the actuator 50 without the actuating stop coming into action. These actuations serve to prime the discharge apparatus in the manner described hereinbefore.

The actuation of an actuator is detected by means of the dosing sensor 40, which is placed in the actuator 50 in such a way that an actuation of the latter exceeding a specific amount is detected. The sensor is preferably constructed as a switch or keying switch, which is switched by a relative position change between the actuator 50 and the casing 11.

If the actuator is actuated, the dosing sensor 40 is operated and a corresponding switching signal is generated in the control unit 70. A check is then made to establish whether at least one preset time interval was exceeded since the preceding actuation of the actuator 50. If this is not the case the electromagnet is activated in such a way that the actuating stop with its blocking member 74 is brought into the blocking position 72. Otherwise the relay is controlled in such a way that the blocking member 74 is brought into the release position 71. If an actuation of the actuator 50 is permitted, then simultaneously the timer for monitoring the time interval since the last actuation of the discharge apparatus is again reset to zero. Obviously monitoring can also incorporate a timer which instead of incrementing, decrements back to zero. Simultaneously with the bringing of the blocking member 74 into the release position 71 or blocking position 72 an alarm signal can be generated by means of a signal generator, the signal preferably being an acoustic signal.

This procedure corresponds to the construction of the blocking member 74 as a bistable element. However, if it is constructed as a monostable element and is e.g. held by an accumulator either in the blocking position 72 or the release position 71, an actuation of the electromagnet must only take place when there is to be a changeover of the blocking member.

Biasing of the monostable blocking member 74 in the release position 71 has the advantage that in the case of a failure of the electronics a discharge can take place by actuating the actuator 50 and then, however, an uncontrolled discharge not respecting the spacing of the first time interval.

As opposed to this a biasing of the monostable blocking member 74 in the blocking position 72 prevents this uncontrolled discharge in the case of a fault, but then a discharge respecting the first time interval is impossible due to the blocking position 72 of the blocking member 74. Particularly in this case it is advantageous to provide means (removable securing element), which permit an at least single actuation of the actuator 50, optionally taking account of irreversible damage.

The release position 71 or blocking position 72 of the blocking member 74 is detected by means of control sensors 41. The control sensors 41 are formed from the first or second contact pin pairs, which are contacted by the contact piece 84 and consequently determine the position. By means of the switch 78 it is possible to generate a new start at which the preset number of actuations of the actuator 50 can be performed without intervention by the actuating stop. By means of the interface 89 it is additionally possible to access the control unit and to perform a data communication. It is in particular possible to set the parameters of the control unit 70 and to read out the detected data concerning the use of the discharge apparatus.

What is claimed is:

1. Discharge apparatus for media for spraying a fluid optionally containing a pharmaceutical substance, wherein when the discharge apparatus is used, in the actuation of the discharge apparatus in each case an actuating stroke of an actuator with respect to the discharge apparatus casing is performed, wherein a gravity dependent blocking means is provided by which an actuation stroke can be blocked.

2. Discharge apparatus according to claim 1, wherein the gravity dependent operating blocking means includes a movably mounted, mechanical operating means.

3. Discharge apparatus according to claim 2, wherein the operating means are guided in such a way that under a preset spatial orientation of the discharge apparatus the operating means block an actuating stroke of the actuator (50).

4. Discharge apparatus according to claim 2, wherein the operating means are balls (61) guided in a curved path (62).

5. Discharge apparatus according to claim 4, wherein the diameter of the balls (61) is smaller than the path of an actuating stroke.

6. Discharge apparatus according to claim 4, wherein the diameter of the ball (61) almost corresponds to the path of an actuating stroke.

7. Discharge apparatus according to one of the claim 4, wherein the curved path (62) is formed by an inclined plane (63).

8. Discharge apparatus according to one of the claim 4, wherein the curved path (62) has at least one dwell trough (65) defining a holding position and serving to receive the balls (61).

9. Discharge apparatus according to claim 8, wherein a dwell trough (65) is formed in the area of the curved path (62) in which the balls (61) block an actuating stroke of the actuator.

10. Discharge apparatus according to claim 2, wherein at least two operating means movable in different, independent directions are provided.

11. Discharge apparatus according to claim 2, wherein the operating means in each case have on one side a stop member (66) and wherein on the side of the operating means remote from the stop member (66) is the position blocking the actuating stroke of the actuator.

12. Discharge apparatus according to claim 11, wherein in each case one pair of operating means are provided and their stop members (66) are formed on opposite sides of the actuating path.

13. Discharge apparatus according to claim 1, wherein the gravity dependent blocking means block an actuating stroke if the divergence of the orientation of the discharge apparatus from the vertical exceeds an angle of at least 30°.

14. Discharge appartus according to claim 13, wherein the blocking means block an actuating stroke if the divergence of the orientation of the discharge apparatus from the vertical exceeds an angle of at least 45°.

* * * * *

UNITED STATES PATENT AND TRADEMARK OFFICE
CERTIFICATE OF CORRECTION

PATENT NO. : 6,427,684 B2
DATED : August 6, 2002
INVENTOR(S) : Ritsche et al.

It is certified that error appears in the above-identified patent and that said Letters Patent is hereby corrected as shown below:

Column 2,
Line 29, "FIGS. 3a-3e" should be -- FIGS. 3a-3c --

Column 4,
Line 2, "bothsides" should be -- both sides --
Line 13, "nember" should be -- member --
Line 26, "greferably" should be -- preferably --
Line 28, "acapacitor" should be -- a capacitor --

Column 5,
Line 13, "sinplest" should be -- simplest --
Line 30, "ofthe" should be -- of the --

Column 6,
Line 46, "slieder 19" should be -- slider 19 --

Column 7,
Line 27, "outerpart" should be -- outer part --
Line 41, "anactuation" should be -- an actuation --

Signed and Sealed this

Eighth Day of July, 2003

JAMES E. ROGAN
*Director of the United States Patent and Trademark Office*